(12) United States Patent
Chen

(10) Patent No.: US 9,443,665 B2
(45) Date of Patent: Sep. 13, 2016

(54) NANOBIOMIMETIC SUPERCAPACITORS WITH HIGH RATE HIGH ENERGY STORAGE

(71) Applicant: Ellen T. Chen, Germantown, MD (US)

(72) Inventor: Ellen T. Chen, Germantown, MD (US)

(*) Notice: Subject to any disclaimer, the term of this patent is extended or adjusted under 35 U.S.C. 154(b) by 614 days.

(21) Appl. No.: 13/919,222

(22) Filed: Jun. 17, 2013

(65) Prior Publication Data
US 2014/0104751 A1 Apr. 17, 2014

Related U.S. Application Data

(60) Provisional application No. 61/660,059, filed on Jun. 15, 2012.

(51) Int. Cl.
| | |
|---|---|
| H01G 9/00 | (2006.01) |
| H01G 11/52 | (2013.01) |
| H01G 11/02 | (2013.01) |
| H01G 11/04 | (2013.01) |
| H01G 11/26 | (2013.01) |
| H01G 11/48 | (2013.01) |
| B82Y 5/00 | (2011.01) |
| B82Y 30/00 | (2011.01) |

(52) U.S. Cl.
CPC .............. *H01G 11/52* (2013.01); *H01G 11/02* (2013.01); *H01G 11/04* (2013.01); *H01G 11/26* (2013.01); *H01G 11/48* (2013.01); *B82Y 5/00* (2013.01); *B82Y 30/00* (2013.01); *Y02E 60/13* (2013.01)

(58) Field of Classification Search
CPC ...... H01G 11/52; H01G 11/22; H01G 11/32; H01G 9/155
See application file for complete search history.

(56) References Cited

U.S. PATENT DOCUMENTS

| | | | | |
|---|---|---|---|---|
| 6,491,789 B2* | 12/2002 | Niu | ........................ | H01G 9/155 162/145 |
| 8,339,769 B2* | 12/2012 | Schott | .................... | H01G 9/008 361/503 |
| 2008/0225464 A1* | 9/2008 | Lashmore | .............. | H01G 9/058 361/502 |
| 2012/0262842 A1* | 10/2012 | Thompson | ............. | H01G 11/04 361/502 |
| 2013/0271090 A1* | 10/2013 | Hunter | ................... | H01G 11/38 320/167 |
| 2014/0340818 A1* | 11/2014 | Xie | ........................ | H01G 11/30 361/502 |

* cited by examiner

*Primary Examiner* — Nguyen T Ha

(57) ABSTRACT

Nanobiomimetic supercapacitors comprise an "Electron Well" and an "Electron-Dam" Membrane Electrode Assembling (MEA); the "Electron-Well" MEA compromises an electrode comprising a substrate of glassy carbon; a self-assembling membrane comprises a polymer matrix; wherein the polymer matrix is comprised of an electrically conductive copolymer; wherein the copolymer is further comprised of one or more first β-cyclodextrin molecules having at least one or more free acetyl groups; one or more polyethylene glycol molecules; one or more poly(4-vinylpyridine) molecules; and one or more second β-cyclodextrin molecules; the self-assembling membrane having a surface structure comprising one or more nanopores and pillars; the nanopores and pillars are vertically oriented on the substrate to form nanopore and pillar array; the "Electron-Dam" MEA compromises the nanopore/pillar layer sealed with an embedded hydrophobic aromatic substance having a flat lid structure; Wherein the MEA can be as either said positive or negative electrode; wherein the "Electron-Well" also can be either said as positive or negative electrode; separated by a porous insulator wetted by an electrolyte-free and air-independent organic solution; at least two current collectors are at each of the end of the MEAs.

38 Claims, 21 Drawing Sheets

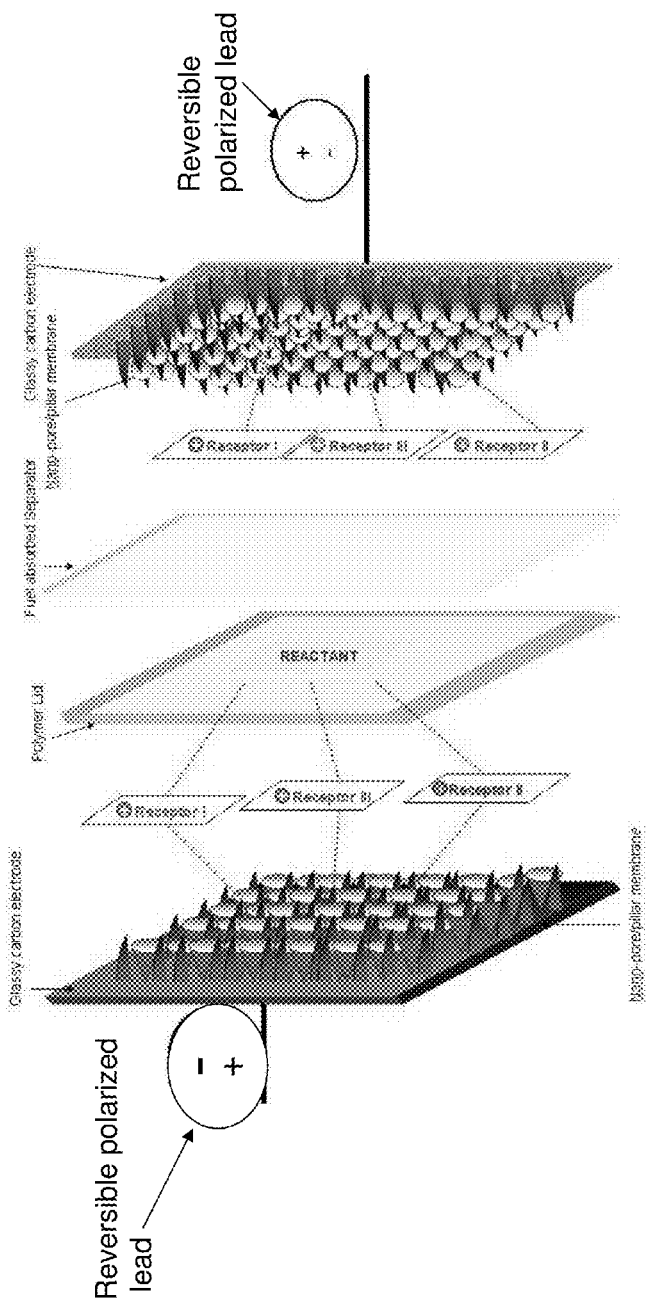

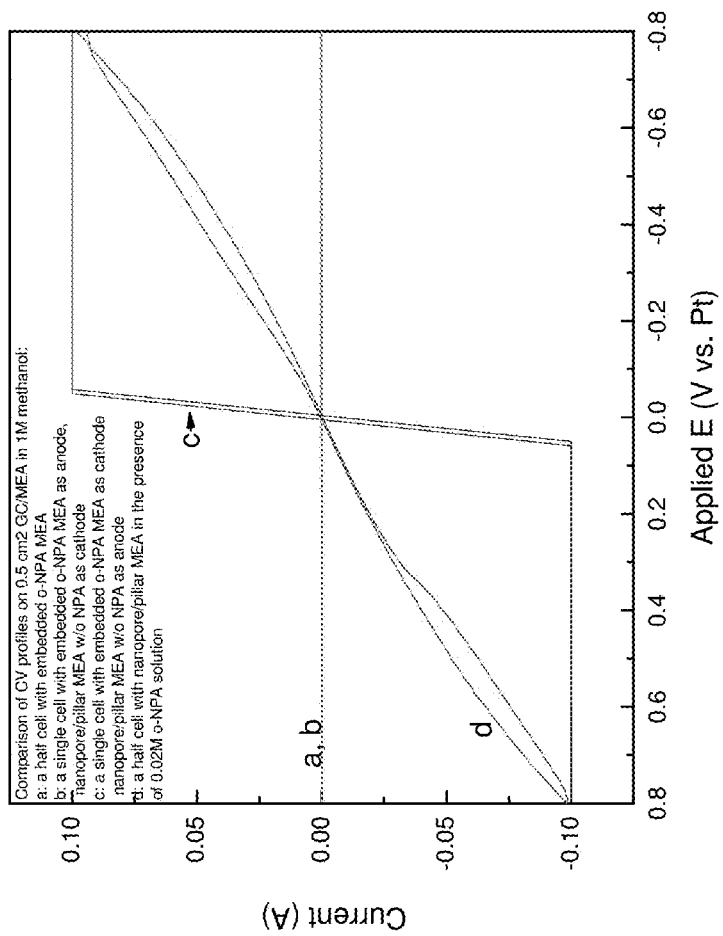

NANOBIOMIMETIC SUPERCAPACITORS WITH HIGH RATE HIGH ENERGY STORAGE

CROSS REFERENCE TO RELATED APPLICATIONS

This application is a nonprovisional of U.S. provisional application No. 61/660,059, filed 15 Jun. 2012 and entitled "Nanobiomimetic Supercapacitors with High Rate High Energy Storage," the disclosure of which is incorporated herein by reference in its entirety.

FIELD OF THE INVENTION

The present invention relates to the field of power and energy, and energy conversion, in particular, to a new generation of nanobiomimetic supercapacitor for bio-mimicking Electrophorus Electricus's Reversible Membrane Potential (RMP) for high rate high energy storage, method of making and uses thereof.

BACKGROUND OF THE INVENTION

Electrophorus Electricus (EE) is know to its discharge electric voltage pauses through multiple organs based on Reversible Membrane Potential (RMP) [see reference 1-2]. Piccolino et al summarized John Wash's studies in electric fish [see reference 3]. Nowadays, researchers are increasingly interested in study of the electric fish and seek a nature inspired way to develop more efficient energy converting devices by developing artificial electric fishes [see reference 4-6]. The article mimicked the biological cell's ion channel functions [see reference 4], or mimicked electric fish's electroreceptive capabilities to find a target without seeing at the deep underwater [see reference 5]. However, there is an important area in multiple-organ discharge that mimics the EE fish's RMP have not been pursued. The EE discharges a small potential at the head, namely Hunter's organ for prey food and also discharges a high voltage at the tail organ, namely Sach for defense purpose. The multiple organ discharge function is based on the RMP. The #1 goal of this invention is to develop an Electron-Relay (ER) prototype supercapacitor that mimics Electrophorus Electricus's reversible membrane potential for multiple-organ discharge under Double-Layer Potential (DLP) negligible, oxygen-independent and electrolyte-independent conditions. The rationale of these settled conditions are based on the needs of many patients who suffer from unbalanced axon action/resting potential due to dysfunction of Ion-channel or ATP pump dysfunction, such as Trauma Brain Injury (TBI), various cancer diseases and chronic illness, such as diabetes. We design an energy platform device without electrolyte-dependence and with minimum DLP that will simplify and eliminate the error source contributions from the device membrane. Air-dependent is common for most nature enzymes; however, it can create a problem of $CO_2$ emission in a closed compartment of underwater vehicles if a nature enzyme used as the source of an energy device. Therefore, using an air-independent nanostructure biomimetic membrane electrode assembling will offer advantages for accomplishing the goal.

Power sources for ammunitions have strict requirements for high rate high energy storage, and especially demands a high Ammunition Gravimetric Energy (AGE) at the first 10 s in the value of 1 kJ/kg energy level [see reference 7]. Current ammunition systems are heavy and occupy large volumes. There is an urgent need to fulfill the US Army's ammunition's demands. Therefore, development of high rate high energy storage devices is critical to support the Army. E. Chen's group recently reported a break-through approach: using an electrolyte-free and air-independent nanobiomimetic membrane electrode assembling (NBMEA) to overcome the drawbacks from conventional approaches and the results with high power density and energy density were reported [see reference 8-9]. However, transferring from a laboratory three-electrode half cell device to a two-electrode prototype device, was blocked by the short discharge time and slow discharge rate. The discharge time was an order of magnitude shorter than 12 hrs in the 1.0 $cm^2$ single cell, and several orders of magnitude shorter for the 0.5 $cm^2$ control under the same experimental conditions reported in E. T. Chen group's works [see reference 8-9], which the Army's AGE and AVE specifications can not be met. The #2 goal of this invention is to develop innovative approaches that overcome the drawbacks and create new prototype Battcells that offer a magnitude increase in performance compared with the controls and provide a means to offer high rate high energy storage device that fulfills the unmet needs.

SUMMARY OF THE INVENTION

It is an object of the present invention to provide a supercapacitor comprising a anode and a cathode electrode and a cyclodextrin forming nanopore and nanopillar membranes and chemically modified to be electrically active affixed to said as membrane electrode assembling (MEA), with or without an embedded "reactant" membrane lid, separated by an insulator, and with current collectors at the two ends when applied a mild potential. The nanopore/pillar structured self-assembling membrane (SAM) supercapacitor can be used for continuously discharge voltage at high rate and the Ammunition Gravimetric Energy (AGE) in the range ≥3 kj/kg($cm^{-2}$) and the Ammunition Volumetric Energy (AVE) in the range ≥5 kj/L under the conditions without metal catalyst and without electrolyte.

It is also an object of the present invention to provide a new generation of electrochemical supercapacitor that has minimum effect of double-layer potential (DLP) and facilities electron-relay among the receptors with or without a polymer lid that are embedding a "reactant" at the two MEA plates, which are based on a unique asymmetric layered engineering design. The new designs overcame the drawbacks of ordinary supercapacitors with slow discharge rate and short discharge time. It is a further object of the present invention to provide a supercapacitor that mimics Electrophorus Electricus's Reversible Membrane Potential (RMP) for multiple-organ discharge under Double-Layer Potential (DLP) negligible, oxygen-independent and electrolyte-free conditions based on a flexible MEA assembling. The Biomimetic EE device has the power and energy density from a single cell is several magnitudes higher than the EE's single electrocyte of 0.03 W/kg and 0.03 Whr/kg, respectively.

It is a still further object of the present invention to provide a supercapacitor that the storage capacity is magnitude higher than the literature reported on DLP supercapacitor at 120 Hz and the invented supercapacitor offers a wider linear working frequency window over 0.015 to 1000 Hz.

It is a still further object of the present invention to provide a method for measuring the electric potential discharge with single or double step chronopotentiometry.

It is a still further object of the present invention to provide a method for constructing a supercapacitor comprising the step of contacting two MEAs separated with a wetted insulator comprising poly cellulortes membrane to form micro pore structures. In preferred embodiments, the membrane of the MEA constitutes of chemically modified cyclodextrin may be triacetyl modified -β-cyclodextrin and it forms self-assembling nanopore/pillar structure membrane in one MEA, and at another MEA plate, it has a lid polymer "reactant" membrane without nanopore/pillar structure together with PEG (polyethylene glycol) and PVP (poly(4-vinylpyridine)).

BRIEF DESCRIPTION OF THE DRAWINGS

FIG. 2 illustrates the asymmetric design of the electron-relay nanobiomimertic supercapacitor.

FIG. 3 illustrates the characterization of the surface morphology using the AFM method. The AFM characterization of the membranes.

FIG. 4 Plots of Cyclic Voltammagrams of the Biomimetic EE device

DETAILED DESCRIPTION OF THE INVENTION

Example 1

Asymmetric Construction of Supercapacitors

Figure 1:
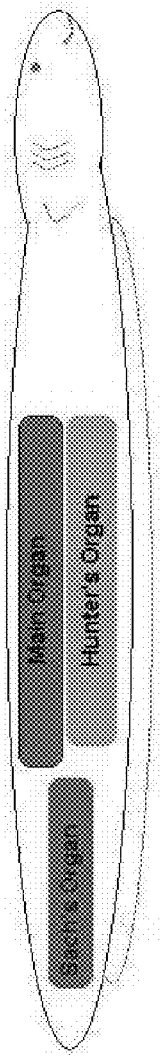
FIG. 1 illustrates the EE's multiple-organ discharges at Sach and Hunter organs.
Figure 3A:
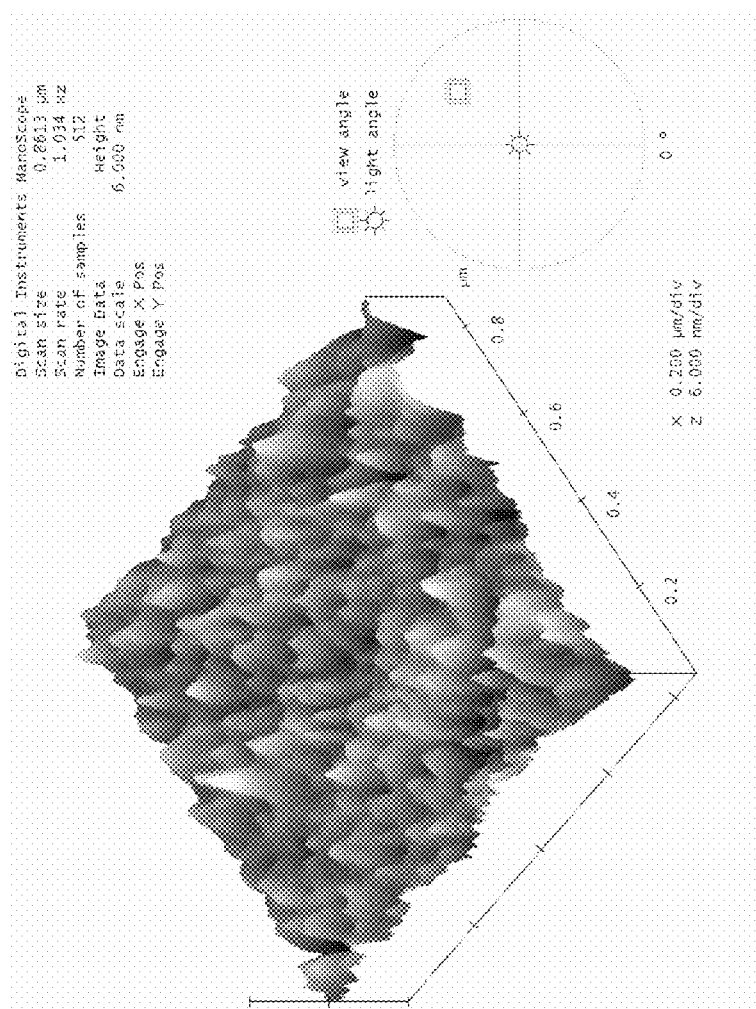
FIG. 3A depicts the nanopillars and nanopores on a GC electrode prior embedded a "reactant" of o-NPA (2 mm in thickness of the electrode). The nanopillars and nanoporous can be seen. Nanopillars are in the range of 10-40 nm in diameter with an average length (z direction) 2-4 nm. The pores are in the range of 50-60 nm in diameter.
Figure 3B:
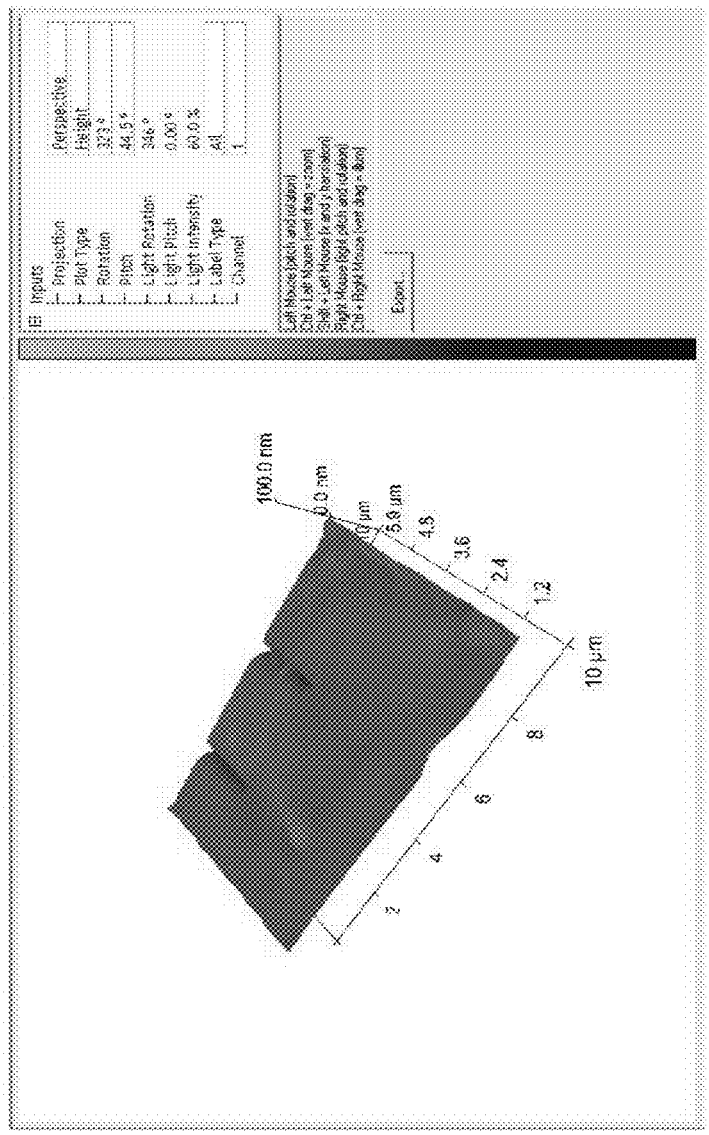
FIG. 3B depicts the AFM image in a diagonal angle view after an embedded "reactant" was added with 48 nm membrane thickness revealed the flat and poreless structure. The two cuts shown due to the laser saw cutting.
Figure 3C:
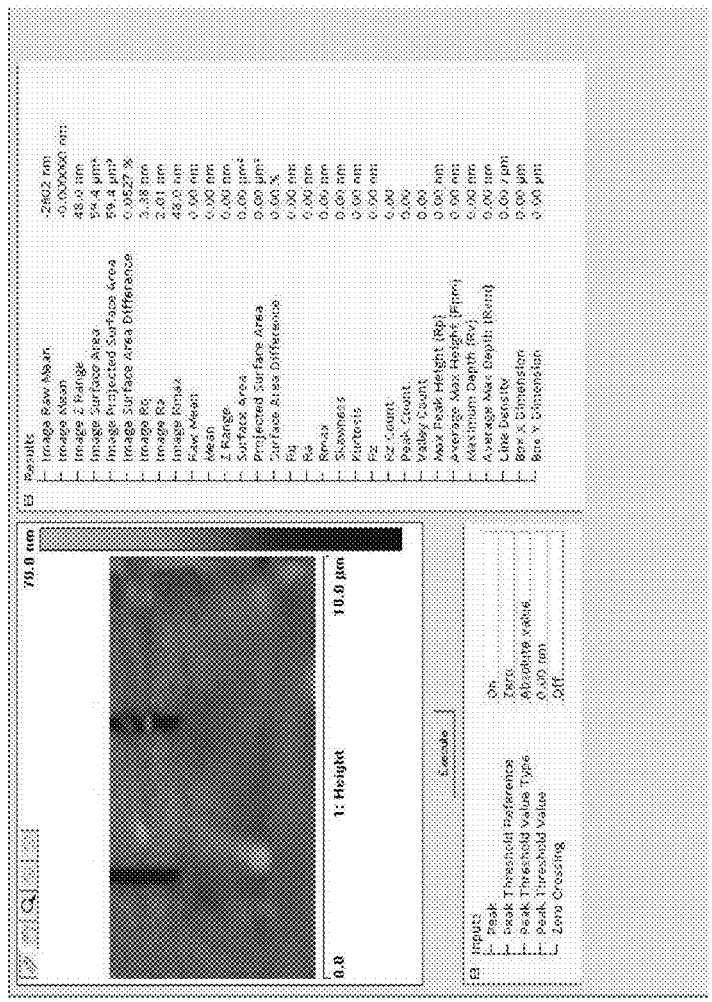
FIG. 3C depicts the AFM section analysis results for FIG. 3B.
Figure 3D:
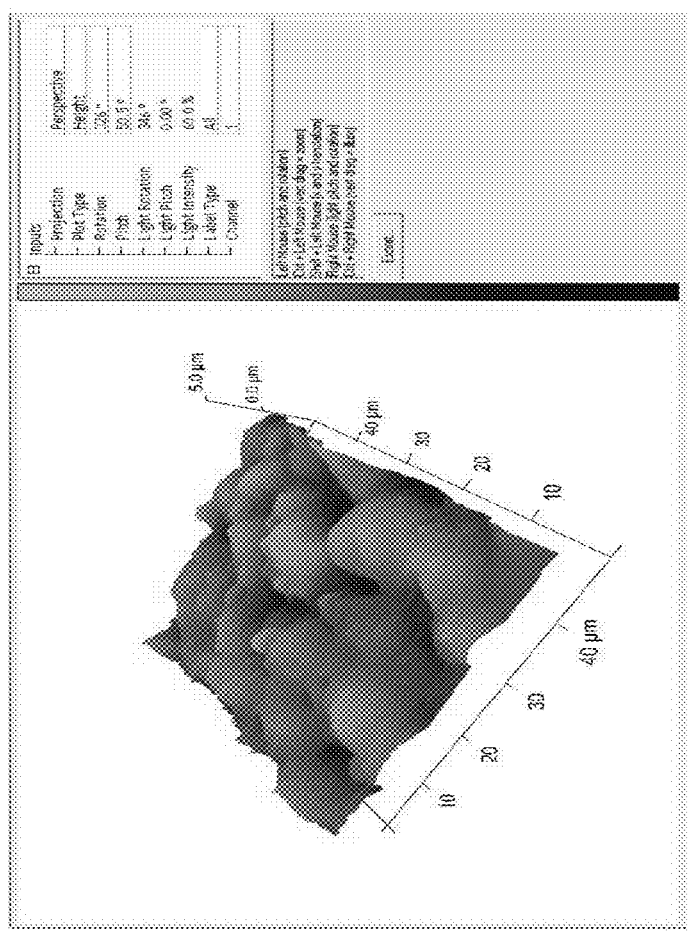
FIG. 3D depicts the AFM image in a diagonal angle view after an embedded "reactant" was added with 5.4 μm film thickness.
Figure 3E:
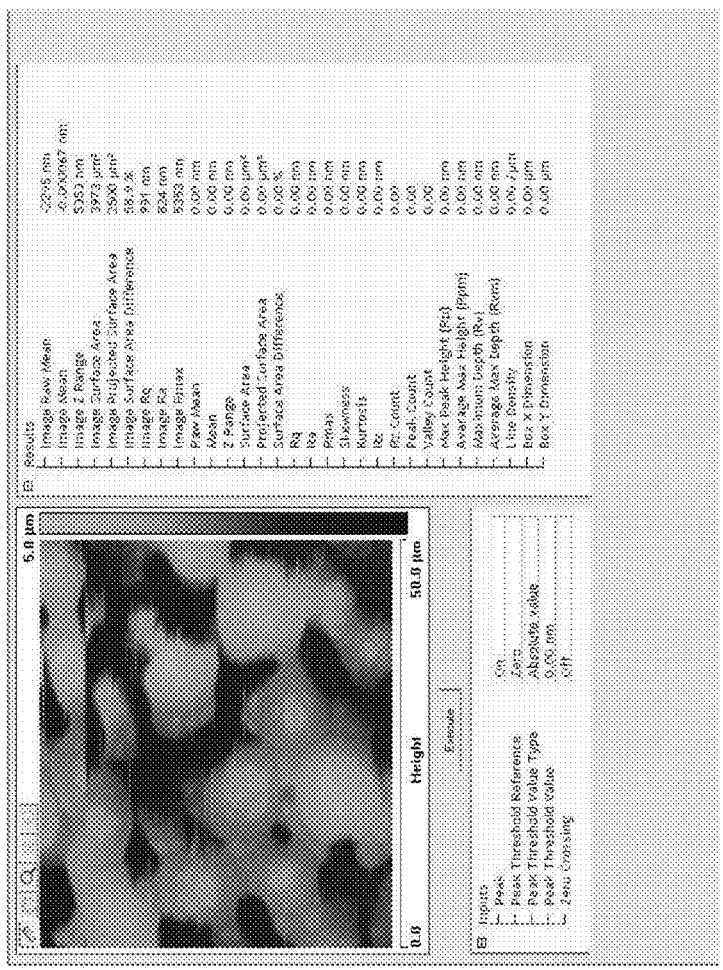
FIG. 3E depicts the AFM section analysis results for FIG. 3D.

Supercapacitors have two categories by energy storage mechanism: electrochemical double-layer capacitors (DLCs) and redox supercapacitors [see reference 10-12]. An approach to overcome the low Gravimetric Energy Density (GED) of the DLS supercapacitor is to use an asymmetric design: 1. the positive electrode has a low degree of polarization, and 2. the negative electrode has a high degree of polarizability in an attempt to enlarge the window of the difference of the potential change during charge and discharge [see reference 12]. After E. Chen's group developed an electrolyte-free and oxygen-independent battery/fuel cell device [see reference 8-9], the GED and the power density performances were superior. However, to develop a prototype supercapacitor with a RMP property that is capable to mimic the multiple-organ discharge function of the eel fish, we designed a pair of membranes having "Den-well" structure, not only it facilitates the electron-relay among the "Den" with build-in receptors and "reactant", but also the receptors located in the nanopore/pillar "well" structure side of the MEA facilitates the electron-relay as well, hence, the potential difference between the two MEAs may be created by both, the "den-well" structure and the RMP based on the difference of the rate in the electron-relay in the two MEAs. As we recall, E. Chen's report revealed the half cell DMFC is a reversible and rechargeable device [see reference 9 and 13]. The Hunter's organ from the eel fish can discharge voltage from the head in a small amplitude of 10V for matting purpose, and the Sach's organ at the tail can discharge high voltage in the amplitude of 250-500 V for defense and preying food [see reference 14-15] as shown in FIG. 1. The asymmetric design of the supercapacitor was illustrated in FIG. 2. One GC electrode with self-assembling (SAM) nanopore/pillar structure and provides the RMP-MEA, and the other GC electrode with an embedded "reactant" flat surface structure SAM with the thickness 48 nm [see reference 9] as another RMP-MEA and an insulator was placed between the two MEAs. The insulator was absorbed with 1M methanol under electrolyte-free and air-independent conditions. The current collectors were attached at each end. Fabrication and characterization using Atomic Force Microscope (AFM) for the two MEA membranes were described elsewhere [see reference 9] see FIG. 3. FIG. 3A illustrates the surface morphology by AFM, the nanopillars and nanopores can be seen. Nanopillars are in the range of 10-40 nm in diameter with an average length (z direction) 2-4 nm. The pores are in the range of 50-60 nm in diameter. FIG. 3B is the AFM image of an embedded "reactant" with 48 nm membrane thickness revealed the flat and poreless structure. The two cuts shown due to the laser saw cutting. FIG. 3C illustrates the cross section analysis.

Example 2

Method to Fabricate the Nano-Structure SAM on GC Electrode

The 1 cm² GC Electrodes were purchased. Polyethylene glycol diglycidyl ether (PEG) was purchased from Sigma. Prepare a T-CD solution (8-10 g/L) in methanol, a poly(4-vinylpyridine) (PVP) solution (0.4-1.0 g/L) in 10 mM 4-(2-hydroxyethyl)-1-piperazine-ethanesulfonic acid (HEPES) that contains 50% methanol and a β-CD copolymer (0.01-0.03 g/ml) in HEPES. All prepared solutions were filtered, sonicated, and degassed. The mixture solution was made of 20-35%:10-20%:25-30%:15-45% (v/v) by T-CD: PEG: PVP: CD polymer, respectively. The 1 cm² GC electrode was cleaned before use by a commonly used procedure. The 200 μL mixture solution was injected onto one side of the surface of the GC electrode in a certified class 100 level of a clean room and was incubated for 48 hrs at 35° C. in an incubator. After that, the SAM/GC electrode was washed by extra pure DI water for 10 minutes, then was re-incubated for 2 hrs at same temperature, and after that, the electrode was stored at room temperature.

Example 3

Fabrication of the Embedded "Reactant" Self-Assembling Membrane (SAM)

The nanostructure Biomimetic membrane without an embedded "reactant" was explained in [0028]. For embedding fabrication was to mix the proper compositions of polymers as [0028] and added "reactant" with 1000:1 molar ratio of triacetyl-β-cyclodextrin (T-CD) into the mixture, and well equilibrium for 2 hrs at 35° C., then directly deposited the mixture onto the surface of the glassy carbon (GC) electrode and incubated for 48 hrs and follow the cited procedures for a complete self-assembling membrane.

Example 4

Characterization of the Membrane of GC-SAM

The morphology of the 1 cm² GC-SAM was characterized by using an instrument (Digital Instruments Nanoscope, Atomic Force Microscope, Veeco Instruments, Calif.). The surface structure was scanned using a silicon cantilever and a tip with 5-10 nm radius. The nanopillars and nanoporous can be seen in FIG. 3A. Nanopillars are in the range of 10-40 nm in diameter with an average length (z direction) 2-4 nm. The pores are in the range of 20-40 nm in diameter. In FIG. 3A is the Atomic Force Microscopy (AFM) image before embedding the "reactant". FIG. 3B is the AFM after embedding the "reactant" with a thinner membrane. The thicker membrane was shown in FIG. 3C, fabricated by dividing a mixture solution into 10 small portions, and depositing consecutively with a drying time of 15 minutes, between each deposit. After that the normal procedures were followed. The thinner membrane was shown in FIG. 3B, fabricated by depositing a mixture solution onto the 1 cm² GC surface at once.

Example 5

Double-Layer Potential (DLP) Effect

Double-layer potential (DLP) effect is the base for most supercapacitors and the interaction of the solvated ions with the charged metal involves only long-range electrostatic forces, so that the interaction is essentially independent of the chemical property of the ions [see reference 16]. The nature of the electrostatic force leads to a quick and short discharge characteristics of the DLP supercapacitors. The good side is its high power density and drawback is the low energy density. Our approach to have an electrolyte-free media has minimized the effect of DLP, hence the reciprocal of the $C_H$ (capacitance at Out Helmholtz Plane (OHP)) value will be increased, and the $C_d$ value will be governed by the smaller item component of the Gouy-Chapman-Stern equation [see reference 16] model, because the $C_D$ (Diffuse layer capacitance) becomes so large by conventional approach at either high electrolyte concentration or very high polarization potential, hence the term of $1/C_D$ is negligible and variable, then the $C_H$ is large (high electrolyte concentration), hence $C_d$ (Differential capacitance at DL) becomes large and in a function of potential at real world situation, the error contributed to the specific capacitance of the supercapacitor will not be negligible.

$$1/C_d = 1/C_H + 1/C_D \qquad (1)$$

Because one usually charges a large constant current to the capacitor, so $$E = i(R_s + t/C_d) \qquad (2)$$

$R_s$ is the resistance of the resistor. i is a constant current, and t is time, E is the voltage. When assumes a constant $C_d$, the potential will be linearly increase with time. Because usually people charge a large current or discharge a large current, so that it could be much larger than the faradic redox current, hence a conventional redox supercapacitor approach with electrochemical reaction takes place and the by-products produced in the supercapacitor reduces the capability to storage charge.

We created the E-R system for the energy storage, many efforts have been made to eliminate the DLP effect and create a unique "supercapacitor" that does not rely on electrolyte and is not dependant on the DLP, nor depending on the chemical reaction, we utilize the model of +COO⁻ (from triacetyl-β-cyclodextrin (T-CD)) . . . o-nitrophenyl-acetate (o-NPA) . . . PEG . . . PVP . . . CD polymer to form the $(PNPN)_n$ type doping in three dimensional layered structure [see reference 13] and the charge stored in the "electric Den" when a small potential is initiated to the supercapacitor, then another MEA has a open electric "well" structure (nanopore/pillar only), and it has COO⁻ (from triacetyl-β-cyclodextrin (T-CD)) . . . PEG . . . PVP . . . CD polymer E-R relay, also forms $(PNPN)_n$ with different potential gradient from the Den, hence electron flow reversibly with fast and quick discharge or charge, yet it has discharge several magnitude longer than ordinary DLP supercapacitor, because there is no heavy $C_H$ and $C_D$ blockage nor leakage. The invention advanced among the well-known supercapacitor configuration using conductive polymers reviewed by G. A. Snook et al [see reference 17]. According to the reference, there are only three types configurations for the supercapacitors made by conducting polymers: type 1. symmetric, using the same p-doping polymers for both electrodes; type 2. asymmetric, using two-different p-doping polymers with a different range of electroactivity; type 3, symmetric, using the same polymer for both electrodes, while the p-doping as the positive electrode, and n-doping as negative electrode [see reference 17]. The drawbacks of the most attractive type 3 configurations can only reach 3V, and did not perform well, due to difficult n-doping process [see reference 17]. Our new invention has revolutionized the configurations of supercapacitor industry by introducing a completely new type of configuration, that is the $(PNPN)_n$ doping with electron-relay and electron delocalization characteristics at both electrodes. Electrons are easy come and go, be stored and be discharged. P. T. Kissinger clearly stated in his book [see reference 18] that there is possible for no chemical reactions taken place at electrodes, but electron lose and gain through redox. As R. A. Huggins stated in the book [see reference 19] that for an electrolyte-depended electrochemical cell, when there is no net flux in the electrolyte, this chemical forces must be balanced by an electrostatic force due to voltage between the electrodes, because $\Delta\mu_i = \Delta G_j$, $\mu_i$ is the chemical potential of species i, $G_j$ is the molar Gibbs free energy of phase j, and the equation is in the integral form. The chemical potential difference between the positive and the negative electrode is balanced by the electrostatic energy, hence $$E = -(RT/z_iF)\ln [a_i^+/a_i^-] \tag{3}$$

$z_i$ is the number of elementary charges carried by particles (ions) of species i, F is Faraday constant, R is the gas constant, T is absolute temperature, $a_i$ is the activity of species a [See reference 19].

According to A. J. Bard et al [see reference 16], the case in a very fast electrode kinetics correspondence to a very large exchange current, in tern it reflects a big intrinsic rate constant $K^0$, that indicates the electrode kinetics requires no driving force at all. FIG. 4 illustrates i-E curves have negligible DLP effect as shown in curve c that such one single cell prototype device is an ideal nonpolarizable device as described in literature with very fast electron exchange rate, there is no kinetic parameters in the Nernst equation (4) for the fast and reversible behavior $$E = E^{0'} + (RT/nF)\ln [C_O(0,t)/C_R(0,t)] \tag{4}$$

$C_O(0,t)$ refers at zero current at time t, the oxidation concentration of the substance, $C_R(0,t)$ refers at zero current at time t, the reduction concentration of the substance, $E^{0'}$ refers to formal potential. Because the interfacial redox kinetics is so fast that activation effect can not be seen [See reference 16].

Curve c also confirms the over potential reached near zero that is the current reported most effective design of the supercapacitor device exists so far, and it offers advantage of smaller size with most efficiency energy storage and discharge for applications in computer and in mobile transportations and portable radio applications. Curve c shows high $K^0$ (an intrinsic standard heterogonous rate constant) with the typical semiconductor behavior illustrated in the same reference. When the two electrodes were switched, it was polarizable as shown in curve b. Curve d shows the half cell behavior acts like a semiconductor switchable at zero potential with the maximum current of ±0.1 A reversible at −0.8 and 0.8V, which indicates the asymmetric design, reached the desired goal under the electrolyte-free, air-independent and DLP negligible conditions. This design paved a foundation for "multiple-organ" discharge with a controllable flexibility and signal intensity.

Example 3

"Multiple-Organ" Discharge

Electrophorus Electricus (EE) is know to its discharge electric voltage pauses through multiple organs based on Reversible Membrane Potential (RMP) [see reference 1-2]. The ionic exchange could be the major source caused the RMP according to R. D. Keynes's hypothesis [See reference 2]. B J. Hawkins et al pointed out that maintaining mitochondrial RMP for human cells are very important to avoid many diseases, such as myocardial infarction, stroke, cancer and neurodegeneration [See reference 20], because these patients' mitochondrial RMP values are usually lose. Using the invented design of the supercapacitor with features of electrolyte-free, and air-independent is to simplify and eliminate the error source contributions from the device membrane, because most patients' ion channels are dysfunction, RMP is dysfunction, hence design a Biomimetic eel fish with no ionic channeling, but a perfect functioning RMP will open a door for errorless monitoring and accurate diagnosis or for an independent implantable device application. Air-dependent is common for most nature enzymes; however, it can create a problem of $CO_2$ emission in a closed compartment of underwater vehicles if a nature enzyme used as the source of an energy device. Therefore, using an air-independent nanostructure biomimetic membrane electrode assembling will offer advantages for accomplishing the goal of this study.

Figure 5:
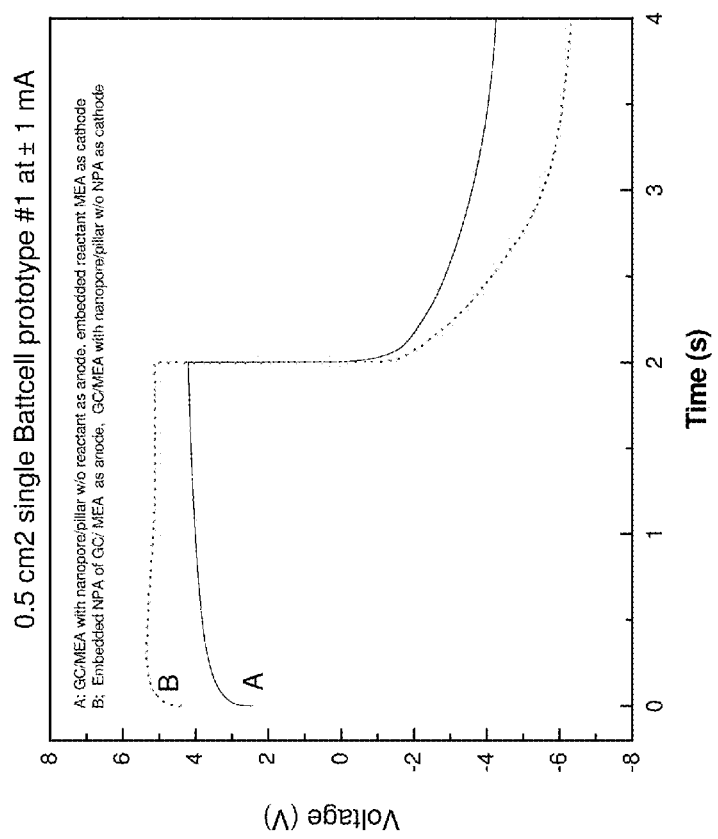
FIG. 5 illustrates the single 0.5 $cm^2$ prototype device's reversible EE membrane charge and discharge behavior.
Figure 6:
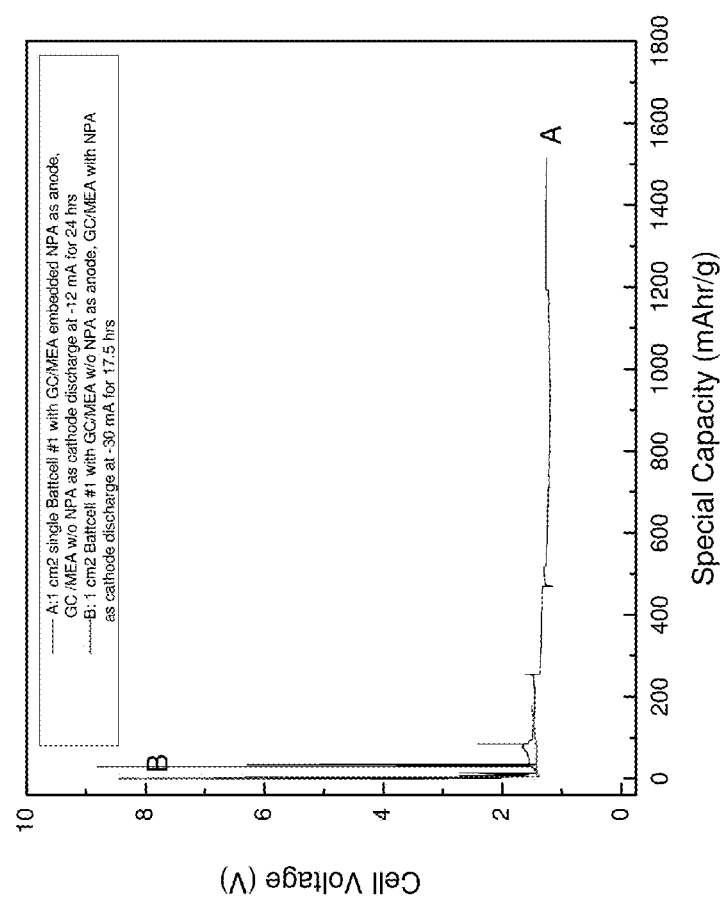
FIG. 6 illustrates a single 1 $cm^2$ prototype reversible membrane discharge.

FIG. 5 illustrates the discharge and charge curves from a single 0.5 cm$^2$ prototype device, A and B curves indicates the "multiple-organ" charge and discharge behavior; FIG. 6 the same behavior is shown for the 1 cm$^2$ single prototype device in discharge with a switchable two ends discharge. The high electric spikes at either end of anode and cathode have a firing rate of 2-fold higher compared with the EE's 3.75V/s [see reference 15]. The power and energy density for a single 0.2 cm$^3$ cell are several magnitudes higher than the EE's single electrocyte of 0.03 W/kg and 0.03 Whr/kg, respectively [see reference 15].

Example 4

Performance of Supercapacitor

Figure 7:
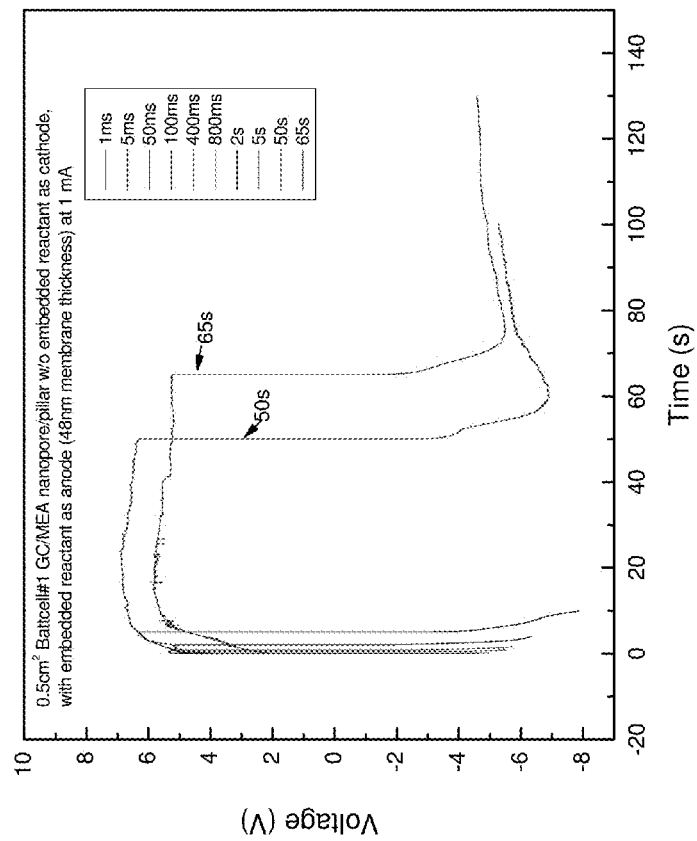
FIG. 7 illustrates the 0.2 $cm^3$ supercapacitor charge/discharge profiles over the band width from 0.015 Hz to 1000 Hz at 10 increment levels.
Figure 8:
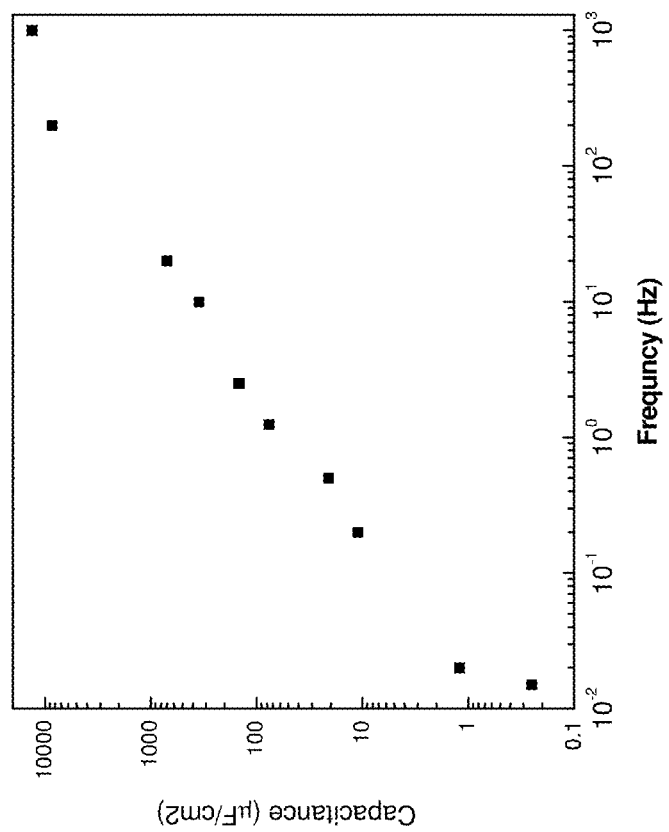
FIG. 8 plot of the capacitance versus frequency (Hz) of the supercapacitor assuming a series RC circuit model.

Based on our asymmetric design of the supercapacitor, the charge/discharge profiles from the 0.2 cm$^3$ prototype supercapacitor is shown in FIG. 7 at 1 mA load over the band width from 0.015 Hz to 1000 Hz at room temperature using the double step chronopotentiometry (DSCPO) method. FIG. 8 is the plot of capacitance vs. frequency that indicates at 120 Hz, the high storage capacity is 5,140 µF/cm2 over the reported data of 175 µF/cm$^2$ of double-layer capacitor [See reference 10], because the 120 Hz filtering to be useful to smoothing the leftover ac ripple on dc voltage busses found in most line-powered electronics for the double-layer (DL) capacitors. The capacitance of the 0.2 cm$^3$ biomimetic EE increased linearly from 0.25 to 13,240 µF/cm$^2$ over a 0.015 to 1000 Hz window, which enables the "multiple-organ" EE not only discharges with power and speed [See Example 3], but also with a high reversible storage capability reported the first time.

TABLE 1

Comparison of performance between the Nano-biomimetic Supercapacitor (NBMSCAP) and the *Electrophorus electricus*

| Name | Discharge rate V/single cell/s. | Discharge location (head) | Discharge location (tail) | Power density (W/kg/single cell or electrocyte) | Energy density Per single electrocyte or cell (Whr/kg) | $O_2$ | Food | Emission $CO_2$ |
|---|---|---|---|---|---|---|---|---|
| NBMSCAP (1)[1] | 4 V/s, 10 V/s | 240 V (60 cell) | 1000 V/100 cell | 20,195.0[7] | 7,474.0[7] | No | No | No |
| *Electrophorus electricus* | 3.75 V/s[2] | 10 V[2] | 500 V/5000 cell | 0.03[5] | 0.03[6] | Yes | Yes | Yes |

[1]Battcell (1) refers to the single 0.5 cm2 prototype device consists of a GC/MEA (48 nm membrane) embedded with o-NPA as anode and another GC/MEA without embedded o-NPA, with nanopore/pillar structure, as cathode, separated by an insulator, and with Pt as current collector. Firing can be at either electrode. Battcell (2) refers to the single 0.5 cm$^2$ prototype device consists of a GC/MEA (48 nm membrane) embedded with o-NPA as anode and another GC/MEA (5.4 μm membrane) with embedded o-NPA, as cathode, separated by an insulator, and with Pt at each end as the current collector. Compared as a control for cell #1.
[2]http://en.wikipedia.org,
[3]Based on 5000 electrocytes.
[4]Simon, Stéphanie; Massoulié, J (1997 Dec. 26). "Cloning and Expression of Acetylcholinesterase from *Electrophorus*". *Journal of Biological Chemistry* 272 (52): 33045-33055.
[5]Based on the Sachs organ, that has 0.15 V discharge rate per electrocyte at the organ weight of ⅓ of 16 kg of the total electric organs weight and divided by 5000 electrocytes at citation 2.
[6]Based on 1 hr discharge capability in citation 2. The mechanism of the discharge from *Electrophorus electricus* is based on the active Ion channels through acetylcholinesterase and ATP[4]. Battcell (1) refers to the single 0.5 cm2 prototype device consists of a GC/MEA (48 nm membrane) embedded with o-NPA as anode and another GC/MEA without embedded o-NPA, with nanopore/pillar structure, as cathode, separated by an insulator, and with Pt as current collector. Firing can be at either electrode. Battcell (2) refers to the single 0.5 cm$^2$ prototype device consists of a GC/MEA (48 nm membrane) embedded with o-NPA as anode and another GC/MEA (5.4 μm membrane) with embedded o-NPA, as cathode, separated by an insulator, and with Pt at each end as the current collector. Firing can be at either side of the electrode.
[7]based on the calculation of a supercapacitor at Liangbing Hua, Jang Wook Choia, Yuan Yanga, Sangmoo Jeongb, Fabio La Mantiaa, Li-Feng Cuia, and Yi Cuia, Highly conductive paper for energy-storage devices, PNAS 106(51), 21490, 2009.

Example 5

Configurations of Making the High AGE Rate Supercapacitors

Figure 9:
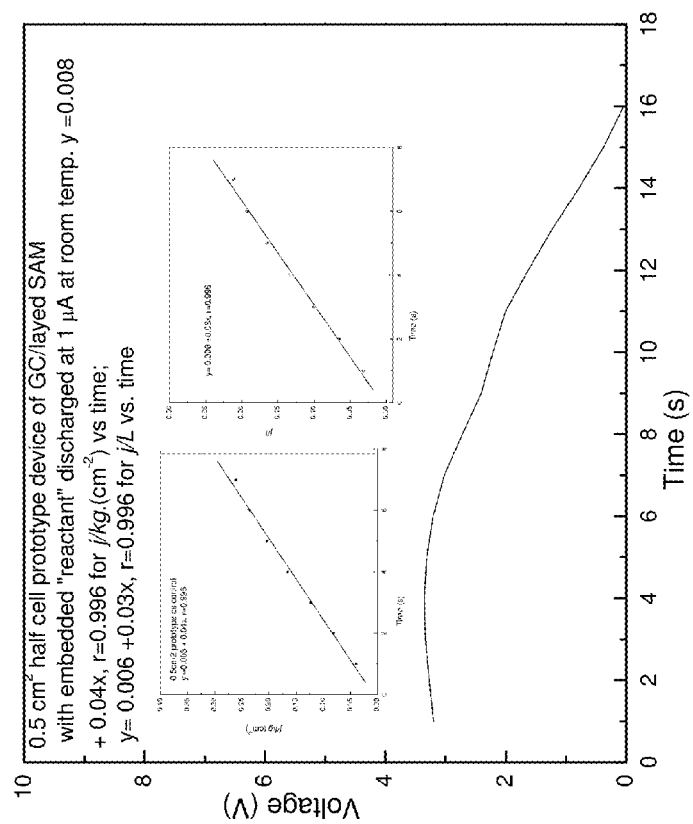
FIG. 9 illustrates the chronopotentiometry curve for a single 0.5 $cm^2$ half cell prototype device discharge at 1 μA at room temperature. Insert left: y (j/kg·$cm^{-2}$)=0.008+0.04x, r=0.996; Insert right: y (j/L)=0.006+0.03x, r=0.996.
Figure 10:
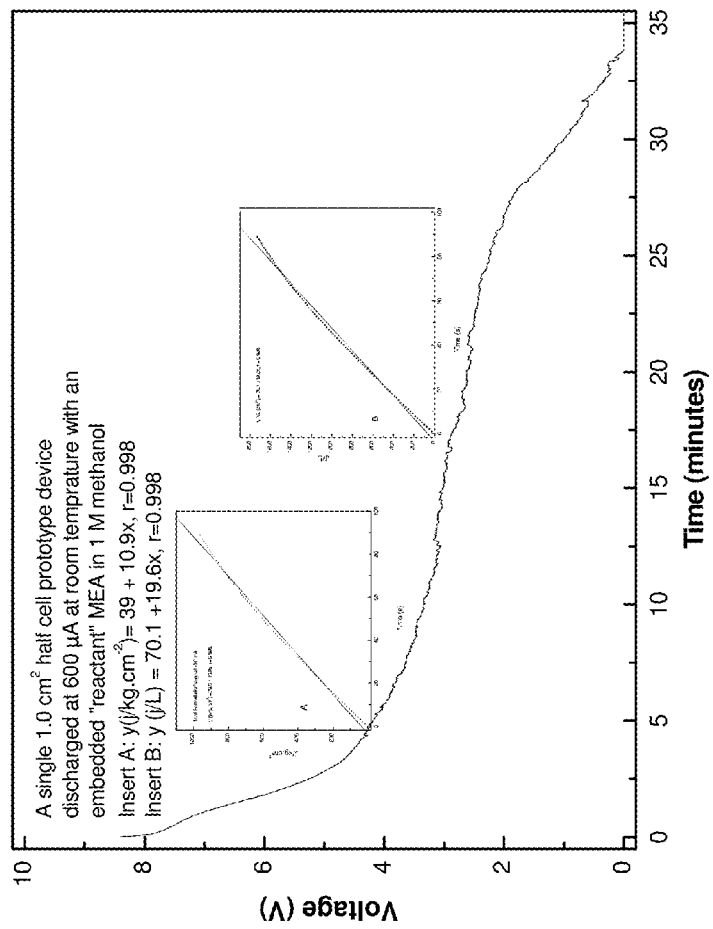
FIG. 10 illustrates the chronopotentiometry curve for a single 1.0 $cm^2$ half cell prototype device discharged at 600 μA at room temperature. Insert A: y (j/kg·$cm^{-2}$)=39+10.9x, r=0.998; Insert B: y (j/L)=70.1+19.6x, r=0.998.

Power sources for ammunitions have strict requirements for high rate high energy storage, and especially demands a high Ammunition Gravimetric Energy (AGE) at the first 10 s in the value of 1 kJ/kg energy level [21]. Current ammunition systems are heavy and occupy large volumes. There is an urgent need to fulfill the US Army's ammunition's demands. Therefore, development of high energy and power density of energy storage devices is critical to support the Army. E. Chen's group recently reported a break-through approach: using an electrolyte-free and air-independent nanobiomimetic membrane electrode assembling (NBMEA) to overcome the drawbacks from conventional approaches and the results with high power density and energy density were reported [8-9]. However, transferring from a laboratory three-electrode half cell device to a two-electrode prototype device, was blocked by the short discharge time and slow discharge rate as shown in FIGS. 9 and 10. The discharge time was an order of magnitude shorter than 12 hrs reported in our prior work for a half cell three-electrode system in the 1.0 cm$^2$ single cell, and several orders of magnitude shorter for the 0.5 cm$^2$ control under the same experimental conditions, which the Army's AGE and AVE specifications can not be met. The goal of this research is to develop innovative approaches that overcome the drawbacks and create new prototype devices that offer a magnitude increase in performance compared with the controls and provide a means to fulfill the unmet needs.

Figure 11:
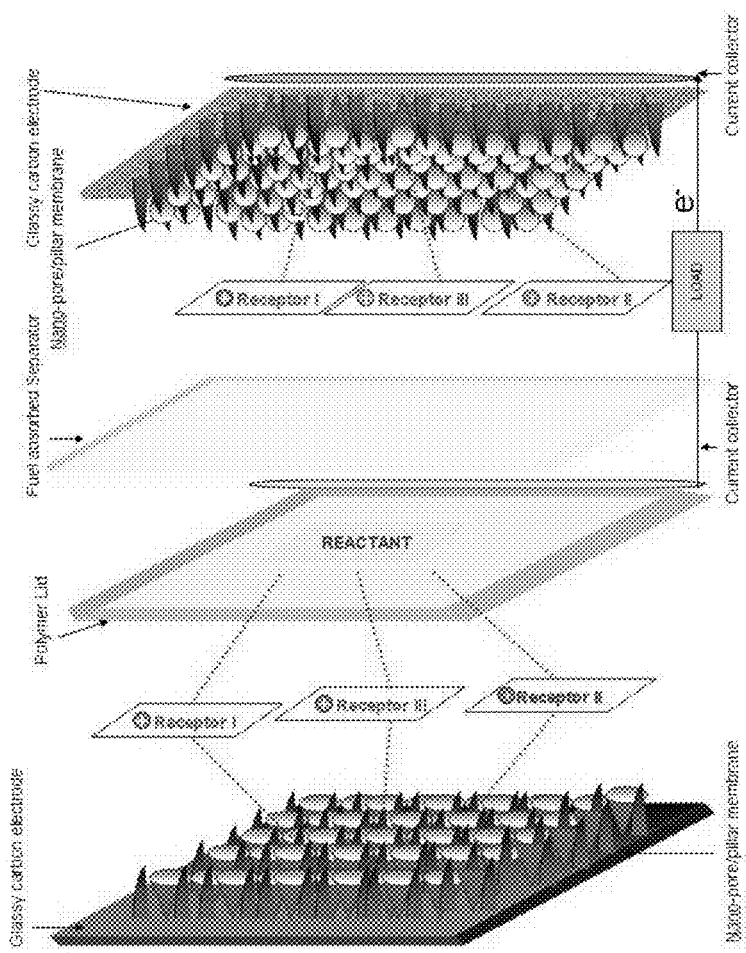
FIG. 11 illustrates an art of the Battcell configuration method #1.
Figure 12:
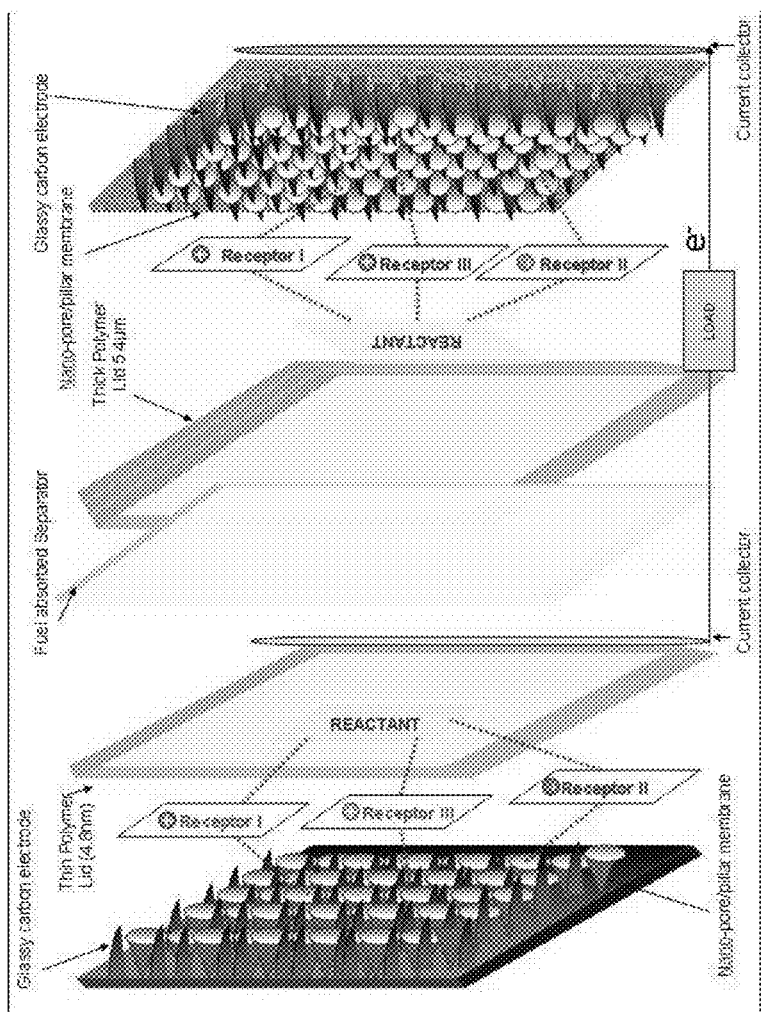
FIG. 12 illustrates an art of the Battcell configuration method #2. Two MEAs have lids on that embedded polymer with "reactant" o-NPA, one lid thickness is 48 nm, and another lid has thickness of 5.4 μm. The separator and the current collectors are same as FIG. 11.

Battcells were configured in two methods. Method #1 configuration was illustrated in art as shown in FIG. 11. The GC/nanopore/pillar structured MEA without an embedded "reactant", and the other GC/MEA was with an embedded "reactant" with a membrane thickness 48 nm [See reference 9]. Inside of the open nanopore/pillar forms "wells" with receptors bearing positive and negative electro-negativity functional groups [See reference 13], that mimic tyrosine kinase domain of Fibroblast Growth Factor (FGF). As we stated in Example 2, under paragraph [0027], the electron flows by the electrochemical potential difference among active receptors embedded in the polymer net work and promoted by the unique nanopore or pillar structures of channeling effect [See reference 22-25], plus the concentration gradient between the solid receptors and the electrolyte-free bulk media when a small potential applied to the cell through a resister. Another MEA with a lid is the "Dam" function, that all electrochemical active receptors not only form electron-relay within the polymer net work, but also form electron-relay with the lid embedded "reactant" as inhibitor, i.e., the Fibroblast growth factor receptor 1 (FGFR1) form complex with an inhibitor—for our case, is o-NPA, an insulator was placed between the two MEAs and absorbed with 1-5 M methanol, preferably 1 M, or pure ethanol under electrolyte-free condition. The current collectors were attached at each end. The method #2 is a symmetric design: two MEAs with embedded "reactant" layered structures as the positive and the negative electrode assembling as shown in FIG. 12 [See reference 9], but the membrane thickness was 48 nm and 5.4 μm [See reference 9], respectively. The cell was tightened and put into a polybag foil (Sigma) and filled nitrogen.

Example 6

Evaluation of the AGE and AVE Performance

The AGE and AVE performance of the Battcell was evaluated using Chronopotentiometry (CPO) method at room temperature under electrolyte-free, catalyst free and oxygen-independent condition. The data was acquired under a constant DC current load, the voltage vs. time data were collected. A linear regression method was used to analyze the rate of AGE and AVE, respectively, by plotting the kj/kg·(cm$^{-2}$) vs. time for AGE and kj/L vs. time for AVE, over the first 1.5 minutes in discharge of a constant DC current. The slope from the linear Least-Square (L-S) regression equation will be the rate for AGE or AVE, respectively. The calculated AGE and AVE values at the first 10 s were obtained through the y values from the linear regression equations, respectively.

Example 7

The Controls

The controls presented in FIGS. 9 and 10 were a single 0.5 and 1.0 cm² half cell prototype device with an embedded "reactant" layered membrane (thickness 48 nm) GC/Self-Assembling Membrane (GC/SAM) separated by an insulator, and the cathode contained no membrane. FIG. 9 shows the discharge curve under 1 µA load for the 0.5 cm² control cell. The discharge curve is illustrated in FIG. 10 for the 1 cm² control cell under a 600 µA discharge load. The inserts are for the initial AGE and AVE discharge rate based on the least-square (L-S) linear regression, respectively. Symbols are for experimental data, and lines are L-S fitted curves. The first 10 s AGE and AVE values were calculated based on the regression equations. The results are listed in Table 1.

Example 8

Battcell Performance of AGE and AVE Results

Figure 13:
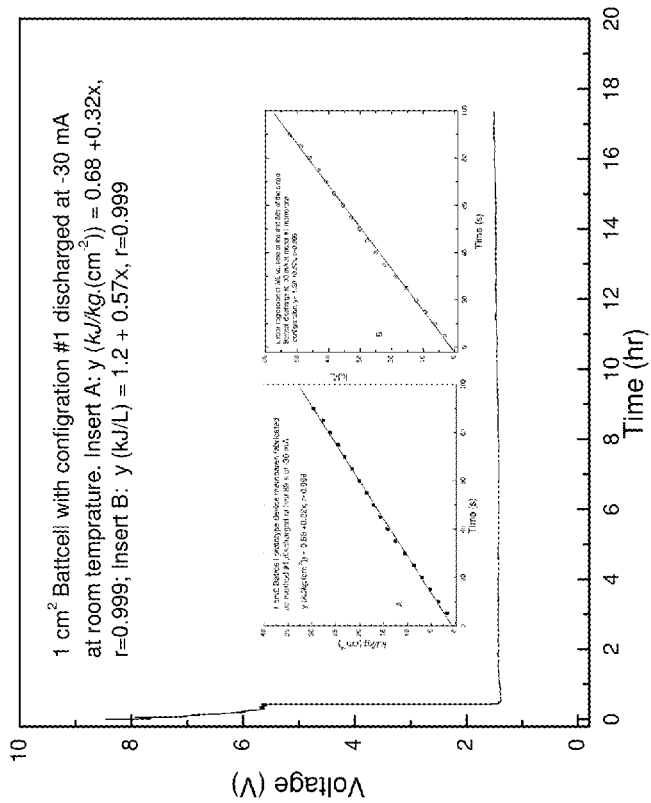
FIG. 13 illustrates the chronopotentiometry curve for the 1.0 $cm^2$ single Battcell prototype device discharge profile at room temperature for method #1 configuration. Insert A is the plot of AGE vs. time; Insert B is the plot of AVE vs. time over the first 1.5 minutes.

FIG. 13 illustrates the 1 cm² Battcell prototype device discharge profile under method #1 configuration. The curve shows there was a deep fast discharge of voltage within the first couple of minutes and then it went to steady-state (s-s) discharge for 17.3 hrs under a 30 mA load. The Insert A and B were for the linear regression curves for AGE and AVE vs. time, respectively. The AGE result at the first 10 s is 3.88 kJ/kg (cm$^{-2}$); the AVE value is 6.90 kJ/L, compared with the control of AGE value of 0.15 kJ/kg·(cm$^{-2}$) and an AVE value of 0.27 kj/L as shown in Table 1. The method #1 configuration for Battcell prototype device has an order of magnitude higher performance than that of the control, and the discharge time of 17.3 hrs, that is 35-fold longer than the control. This indicates the configuration #1 increased the ratio of membrane surface area to volume by using the nanopore/pillar MEA at the anode that extended the discharge time capability at the cathode made by an embedded "reactant" membrane compared with the control. Not only the AVE and AGE values are a magnitude higher for the 1 cm² single Battcell cell, but the specific capacity is 798.5 Ah/kg vs. 0.92 Ah/kg for this Battcell prototype device against the control, that is several orders of magnitude higher capacity.

Figure 14:
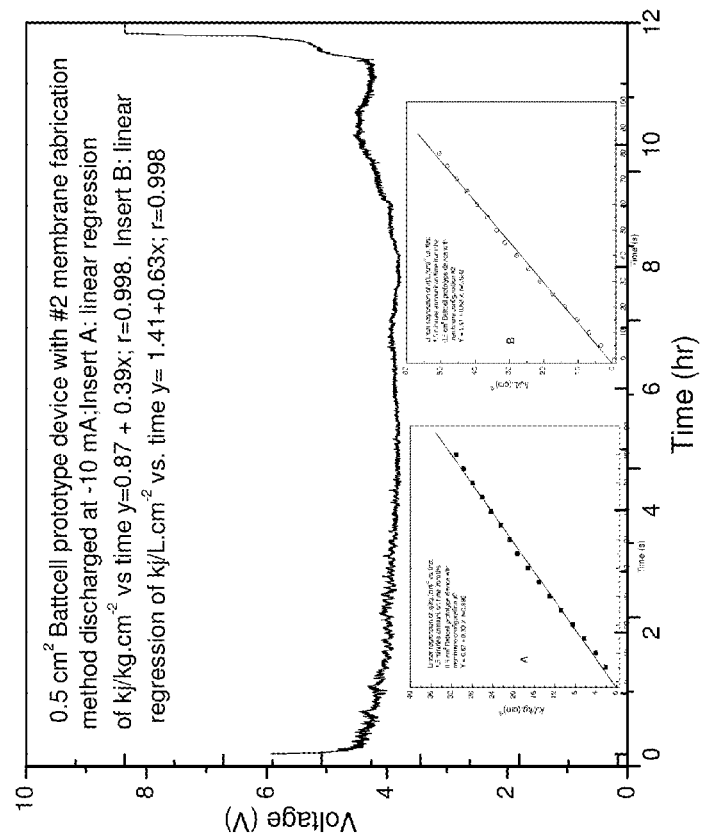
FIG. 14 illustrates the chronopotentiometry curve for the 0.5 $cm^2$ single Battcell prototype device discharge profile at room temperature for method #2 cell configuration. Insert A is the plot of AGE vs. time; Insert B is the plot of AVE vs. time over the first 1.5 minutes.

FIG. 14 illustrates the 0.5 cm² Battcell prototype device discharge profile for method #2 configuration. Insert A is the plot of AGE vs. time; Insert B is the plot of AVE vs. time over the first 1.5 minutes. The Battcell discharge rate of AGE at the transient time is 0.39 kj/kg·(cm$^{-2}$)/s, and the AVE rate is 0.63 kj/L/s from the L-S regression plots as shown in the Inserts. Table 1 is the summary of the results of the performance in AGE and AVE and the corresponding rates. The first 10 s AGE and AVE values were 4.77 kj/kg·(cm$^{-2}$) and 7.71 kj/L, respectively, as shown in Table 1. The specific capacity is 351.7 Ah/kg for the 0.5 cm² Battcell prototype device under method #2 against the control of 0.92 Ah/kg. The results imply that different layer structured membrane thickness between the two MEAs at cathode and anode, with the same embedded "reactant" polymer membranes, increases the difference of the potential gradient due to the thicker membrane, that facilities more receptors than that of the thinner one, hence the nominal potential is 4.7V compared with 1.4V of the method #1 as shown in FIG. 13. Because there was no nanopore/pillar membrane in the method configuration, therefore this 0.5 cm² Battcell prototype with method#2, has half of the capacity than that of the 1.0 cm² Battcell prototype with method#1.

Figure 15:
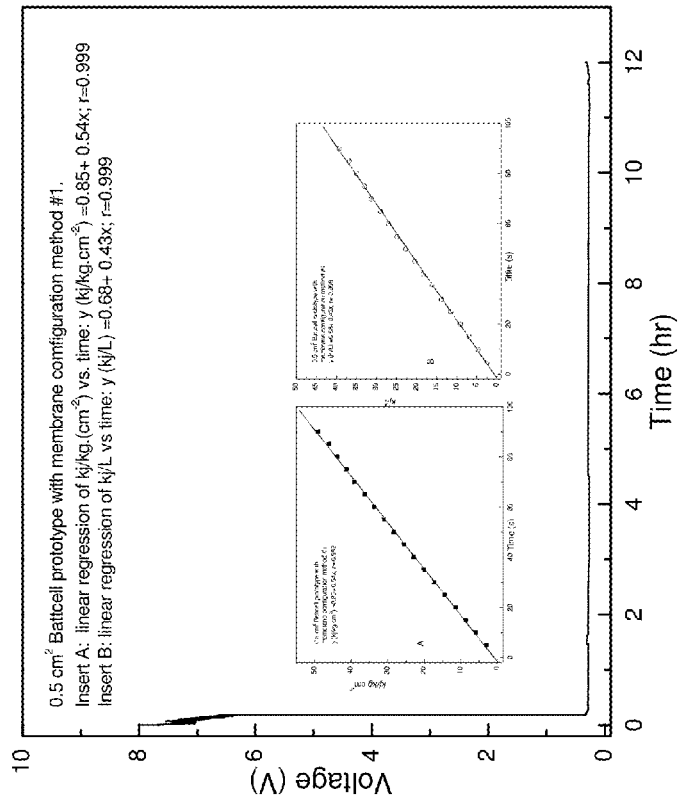
FIG. 15 illustrates the chronopotentiometry curve for the 0.5 $cm^2$ single Battcell prototype device discharge profile at room temperature for method #1 membrane configuration. Insert A is the plot of AGE vs. time; Insert B is the plot of AVE vs. time over the first 1.5 minutes.

FIG. 15 illustrates the 0.5 cm² Battcell prototype device discharge profile at 12 mA for method #1 configuration. The Battcell discharge rate of AGE at the transient time is 0.54 kj/kg·(cm$^{-2}$)/s, and the AVE rate is 0.43 kj/L/s from the L-S regression plots as shown in the Inserts. Table 1 shows the both Battcell method configurations are superior to that of the control. The innovation technology overcame the short discharge time and the slow AGE and AVE rates. Comparing among the two 0.5 cm² Battcell devices, method #1 has higher AGE result than that of method #2, where method #2 has higher AVE value than method #1. This Battcell has specific capacity of 444.4 Ah/kg.

TABLE 1

Comparing of the performance among the single Battcells using different membrane fabrication methods

| MEA size (cm²) | Method | AGE at first 10 s kj/kg · (cm$^{-2}$) (kj/kg · (cm$^{-2}$)/s) | AVE at first 10 s kj/L (kj/L/s) | time (hr) |
|---|---|---|---|---|
| 0.5 | control | 0.41 (0.04) | 0.31 (0.03) | 0.004 |
| 0.5 | #1 | 6.25 (0.54) | 4.98 (0.43) | 12.0 |
| 0.5 | #2 | 4.77 (0.39) | 7.71 (0.63) | 11.8 |
| 1.0 | #1 | 3.88 (0.32) | 6.90 (0.57) | 17.3 |
| 1.0 | control | 0.15 (0.01) | 0.27 (0.02) | 0.5 |

Example 9

Energy Efficiency

Figure 16:
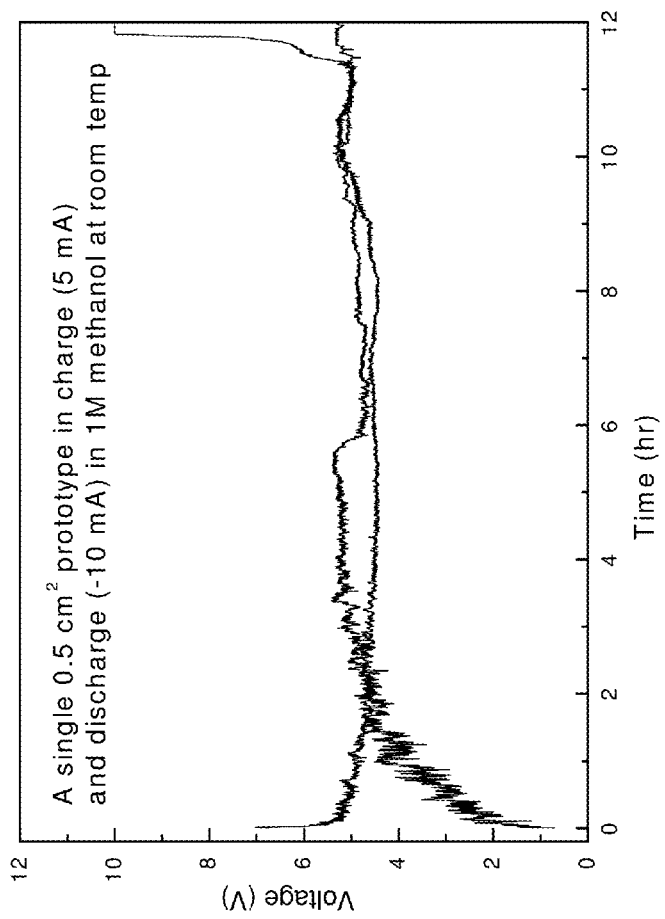
FIG. 16 illustrates the discharge/charge curves of a 0.5 $cm^2$ single prototype supercapacitor with a symmetric "Electron-Dam"-insulator-"Electron-Dam" configuration.
Figure 17:
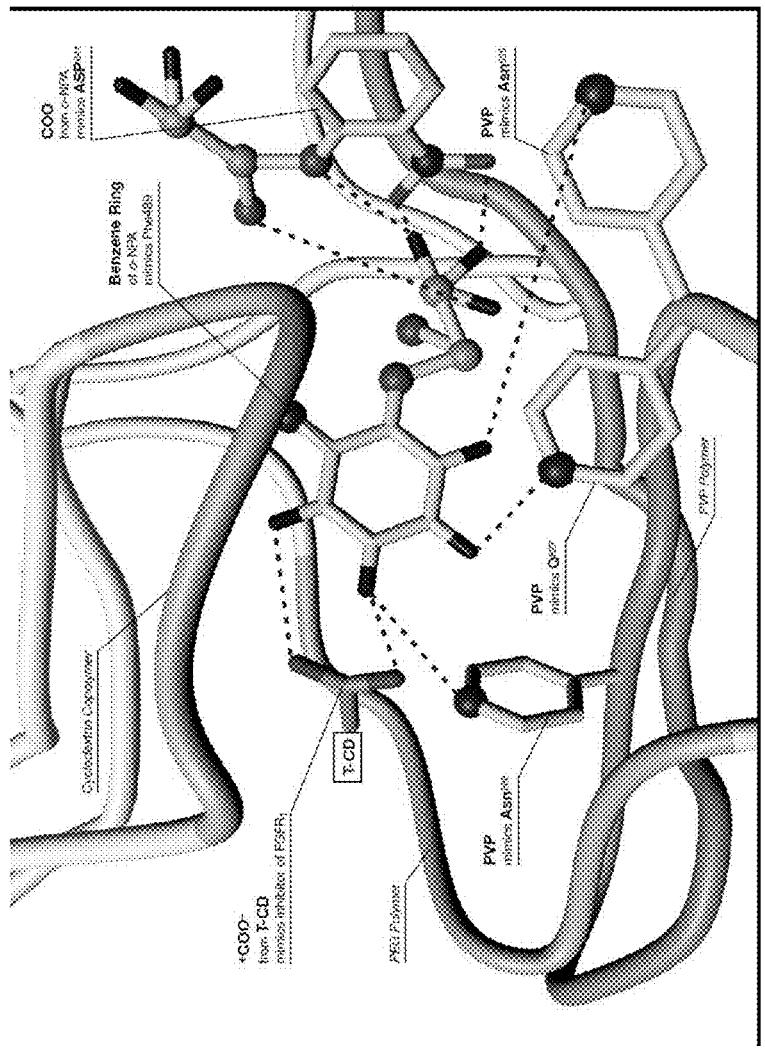
FIG. 17 schematic drawing depicting the biomimetic electron-relay membrane using the structure of the Fibroblast Growth Factor (FGF) receptor 1-inhibitor complex.

FIG. 16 illustrates the discharge/charge curves of a 0.5 cm² single prototype supercapacitor with a symmetric "Electron-Dam$_{thinner}$"-insulator-"Electron-Dam$_{thicker}$" configuration. The energy efficiency is 98%.

CONCLUSIONS

Electrophorus Electricus (EE) is known to discharge electric voltage through multiple organs based on Reversible Membrane Potential (RMP). We report a new type of supercapacitor for mimicking the EE's RMP based on an Electron-Relay Nano-Biomimetic Membrane Electrode Assembling (ERNBMEA) and an asymmetric membrane design with features free from ion channeling effect and a negligible double layer potential effect. The results obtained by a double step chronopotentiometry (DSCPO) method shown the Biomimetic EE devices has the reversible membrane potential in both 0.2 and 0.4 cm³ supercapacitors. It can fire high electric spikes at both ends of the anode and cathode with a firing rate of 2-fold higher compared with the EE's 3.75V/s. The power and energy density for a single 0.2 cm³ cell are several magnitudes higher than the EE's single electrolyte of 0.03 W/kg and 0.03 Whr/kg. The capacitance of the 0.2 cm³ biomimetic EE increased linearly from 0.25 to 13,240 µF/cm² over 0.015 to 1000 Hz range. At 120 Hz, the high storage capacitance is 5,140 µF/cm2 that is an order of magnitude higher over the reported double-layer capacitor.

This invention presents methods for developing high rate high energy storage prototype devices that are electrolyte-free, oxygen-independent and CO₂ emission-free. Method #1 was based on an innovative embedded reactant Membrane/Glassy Carbon (GC) Electrode Assembling (MEA) and a GC/nanopore/pillar membrane MEA design. Method #2 was based on both MEAs embedded with a "reactant", but the membrane thickness was significantly different. Results from single 0.5 and 1.0 cm$^2$ Battcells are presented compared with the control cells that had the same anode MEA, but without cathode membrane. The innovative MEA designs eliminate the drawbacks of short discharge time and low rate in energy storage. The Ammunition Gravimetric Energy (AGE) at the first 10 s is 3.88 kJ/kg for a 1 cm$^2$ Battcell prototype device configured with method #1 compared with 0.15 kJ/kg for the control; the highest Ammunition Volumetric Energy (AVE) is 7.71 kJ/L for the 0.5 cm$^2$ Battcell device with method #2 configuration compared with 0.31 kJ/L from the control. The discharge time from all sized Battcells was at least an order of magnitude higher than that of the controls.

The method #1 and #2 Battcell configurations provide means to overcome the shortcomings of short discharge time and small AGE and AVE values by:

1. Increase the ratio of the membrane surface area to volume through the nanopore/pillar structured membrane.
2. Increase the difference of the potential gradient between the anode and cathode through enlarge the difference of the membrane thickness under same membrane configurations, except the active receptors at one MEA were more than other MEA.
3. The "Electron Dam"-"Electron well" pair design for the supercapacitor has more specific capacity and higher AGE rate than "Electron Dam"-"Electron Dam" configuration.
4. The "Electron Dam"-"Electron Dam" configuration has higher nominal cell potential than that of the "Dam-well" configuration.

Therefore this innovative technology could solve the US Army's unmet needs in high AGE and AVE demands. The wide applications of the invention are not only in supercapacitor and semiconductor industries for revolutionary computer chip designs, but also applications are in transportations, hand-hold radio applications, in ammunition usages and as a unique battery used in medical diagnostic devices.

REFERENCES

[1] M. Altamirano, C. W. Coates, H. Grundfest and D. Nachmansohn, *Mechanism of bioelectric activity in electric tissue*, J. General Physiology, 91, 1953.

[2] R. D. Keynes, H. Martins-Ferreira, *Membrane potentials in the electroplates of the electric eel*, J. Physiol. 119, 315-351, 1953.

[3] M. Piccolino and M. Bresadda, *Drawing a spark from darkness: John Wash and electric fish*, Trends in Neurosciences 25 (1), 51, 2002.

[4] J. Xu, T. K. Vanderlick, D. A. Lavan, *Energy conversion in protocells with natural nanoconductors*, International J. of Photoenergy, Doi: 10.1155/2012/425735

[5] J. Friedman, D. Tones, T. Schmid, J. Dong and M. B. Srivastava, *A Biomimetic quasi-static electric field physical channel for underwater ocean networks*, ACM Workshop, 2010.

[6] J. Xu, F. J. Sigworth, D. A. Lavan, *Synthetic protocells to mimic and test cell function*, Advanced Materials, 22(1), 120-127, 2010.

[7] US Army "High rate high energy storage devices" SBIR A11-119.

[8] E. Chen and R. Finkelstein, *Development of an Electrolyte-free, Oxygen-free, High-Performance Single Direct Methanol Fuel Cell (DMFC)*, 44th Proceedings of Power Sources Conference, 333-336, (2010).

[9] E. Chen and C. Ngatchou, *Study of the Factors that Effect on the Power Storage and Generation of a Nano-Biomimetic Membrane Electrode-Assembling (NBMEA) for Battery/Fuel Cell Dual Applications*, Clean Technology 204-207, (2011).

[10] J. R. Miller and R. A. Outlaw and B. C. Holloway, *Graphene double-layer capacitor with ac line-filtering performance*, Science, 329, 1637, 2010.

[11] L. Zheng, Y. Wang, X. Wang, X. Wang, H. An, and L. Yi, *The effects of surface modification on the supercapacitive behaviors of carbon derived from calcium carbide*, J. Mater Sci 45, 6030, 2010.

[12] S. M. Lipka, J. R. Miller, T. D. Xiao, J. X. Dai, *Asymmetric electrochemical supercapacitor and method of manufacture thereof*, US2009/0290287

[13] E. Chen, *Apparatus and method for high performance fuel cells based on a biomimetic electro-relay membrane electrode assembling*, PCT application was published PCT/US11/34347, on Nov. 3, 2011.

[14] M. Piccolino and M Bresadola, *Drawing a spark from darkness: John Walsh and electric fish*, TRENDS in Neurosciences 25(1), 51, 2002.

[15] http://en.wikipedia.org

[16] Allen J. Bard and Larry R. Faulkner, *Electrochemical Methods, Fundamentals and Applications*, John Wiley & Sons, New York, (1980).

[17] G. A. Snook, P. Kao and A. S. Best, *Conducting-polymer-based supercapacitor devices and electrodes*, Journal of Power Sources, doi10.1016, 2010.

[18] P. T. Kissinger and W. R. Heineman, *Laboratory Techniques in Electroanalytical Chemistry*, Second Edition, Marcel Dekker, New York, (1996).

[19] R. A. Huggins, Energy Storage, Chapter 10, *Principles determining the voltage and capacities of electrochemical cells*, Springer Science * Business Media, LLC, 2010.

[20] B. J. Hawkins, M. D. Levin, P. J. Doonan, N. B. Petrenko, C. W. Davis, V. V. Patel and M. Madesh, *Mitochondrial complex II prevents hypoxic but not calcium—and proapoptotic Bcl-2 protein-induced mitochondrial membrane potential loss*, J. of Biological Chem. 285, 26494, 2010.

[21] US Army "High rate high energy storage devices" SBIR A11-119. 2011.

[22] E. Chen, Nanopore Structured Electrochemical Biosensor, issued by the USPTO U.S. Pat. No. 8,083,926, Dec. 27, 2011.

[23] Ellen T. Chen, C. Ngatchou and K. Bowen, *Development of A Nano-Biomimetic Battery/Fuel Cell (Battcell) Prototype Device For High Power Storage and High Energy Density*, 45$^{th}$ Power Source Conference, accepted, will be published in Jun. 6, 2012 in the Proceedings of the 45$^{th}$ Power Sources Conference, 2012.

[24] Ellen T. Chen*, C. Ngatchou, *An Electron-Relay Prototype Supercapacitor Mimics Electrophorus Electricus's Reversible Membrane Potential for Multiple-organ Discharge*, accepted and will be published in Clean Tech, in Jun. 18, 2012.

[25] E. T. Chen1*, Y. Shen J. Thorten, C. Ngatchoul, S-H. Duh, P. T. Kissinger, *A Nanopore Biomimetic device quantitatively detects early stage cancer cells; a Contour Map Multiple Variable Correlation Method assesses the heat of cancer cells released*, accepted and will be published in the journal of Nanotech, in Jun. 18, 2012.

What is claimed is:
1. A nanobiomimetic supercapacitor comprising: an "Electron well" and an "electron-Dam" Membrane Electrode Assembling (MEA); the "Electron-well" MEA compromise an electrode comprising a substrate of glassy carbon; a self-assembling membrane comprises a polymer matrix; wherein the polymer matrix is comprised of an electrically conductive copolymer; wherein the copolymer is further comprised of one or more first β-cyclodextrin molecules having at least one or more free acetyl groups; one or more polyethylene glycol molecules; one or more poly(4-vinylpyridine) molecules; and one or more second β-cyclodextrin molecules; the self-assembling membrane having a surface structure comprising one or more nanopores and pillars; the nanopores and pillars are vertically oriented on the substrate to form nanopore array and pillar array; the "Electron-Dam" MEA compromises the nanopore/pillar layer sealed with an embedded hydrophobic aromatic substance having a flat lid structure; wherein the MEA can be as either said positive or negative electrode; wherein the "Electron-Well" also can be either said as positive or negative electrode; separated by a porous insulator wetted by an electrolyte-free and air-independent organic solution; at least two current collectors are at each of the end of the MEAs.

2. The nanobiomimetic supercapacitor according to claim 1, wherein the "Electron-well" MEA further compromises the average nano-pillars size is the range of 10-40 nm in diameter with an average length (z direction) 2-4 nm the pores are in the range of 20-40 nm in diameter.

3. The nanobiomimetic supercapacitor according to claim 1, wherein the "Electron-well" MEA further compromises multiple n-type and p-type dopants, that form electron-relay between the dopants when a mild potential is applied across the supercapacitor.

4. The nanobiomimetic supercapacitor according to claim 1, wherein the "Electron-well" MEA further compromises a Biomimetic membrane that mimics Fibroblast growth factor receptor (FGFR) 1 of tyrosine kinase domain.

5. The nanobiomimetic supercapacitor according to claim 1, wherein the "Electron-well" MEA further compromises a biomimetic FGFR1 membrane with thickness in the range of 40-500 nm, in a preferred thickness, less than 100 nm.

6. The nanobiomimetic supercapacitor according to claim 1, wherein the medium selected among the organic solutions are methanol or ethanol and the concentration ranges preferably between 1 to 5 M.

7. The nanobiomimetic supercapacitor according to claim 1, wherein the current collectors selected among metals of platinum, stainless steel and platinum alloy.

8. The nanobiomimetic supercapacitor according to claim 1, wherein the "electron Dam" further compromises a flat structure with poreless configuration, preferably pillarless in the membrane thickness range between 50 nm to 5 μm.

9. The nanobiomimetic supercapacitor according to claim 1, wherein the "electron Dam" further compromises a lid material that seals of the nanopore/pillar selected among active material of nitro-phenyl acetate and any aromatic hydrophobic materials.

10. The nanobiomimetic supercapacitor according to claim 1, wherein the "Electron Dam" further compromises n-type and p-type dopants, that form electron-relay between the dopants when a mild potential is applied across the supercapacitor.

11. The nanobiomimetic supercapacitor according to claim 1, wherein the "Electron Dam" MEA further compromises biomimetic FGFR1-inhibitor complex membrane with thickness in the range of 0.05-6 μm.

12. The nanobiomimetic supercapacitor according to claim 1, wherein the "Electron Dam" MEA further compromises the biomimetic membrane is a self-assembling membrane.

13. The nanobiomimetic supercapacitor according to claim 1, wherein has a reversible membrane potential.

14. The nanobiomimetic supercapacitor according to claim 13, wherein leads to electrophorus electricus (EE)-like "multiple-organ" discharge.

15. The nanobiomimetic supercapacitor according to claim 14, wherein the discharge rate at 4V/s and 10V/s at "head" and "tail", respectively that is better than the EE of 3.75V/s.

16. The nanobiomimetic supercapacitor according to claim 13, wherein the power density of 20.2 kW/kg from 0.2 $cm^3$ single cell and energy density of 7.5 kWh/kg of the single cell.

17. The nanobiomimetic supercapacitor according to claim 13, wherein is ion channel effect free.

18. The nanobiomimetic supercapacitor according to claim 1, wherein has negligible effect from double layer potential.

19. The nanobiomimetic supercapacitor according to claim 1, wherein the capacitance of the 0.2 $cm^3$ biomimetic EE increased linearly from 0.25 to 13,240 $\mu F/cm^2$ over a 0.015 to 1000 Hz window, which has highly reversible storage capability.

20. The nanobiomimetic supercapacitor according to claim 1, wherein at the useful industry application frequency 120 Hz, the high storage capacity is 5,140 $\mu F/cm^2$, that is 50-fold over the DLP supercapacitors.

21. The nanobiomimetic supercapacitor according to claim 1, wherein another symmetric configuration of "Electron-Dam"-insulator-"Electron-Dam" also works with high nominal discharge voltage, except the "Electron-Dam"-insulator-"Electron-Well" asymmetric configuration.

22. The nanobiomimetic supercapacitor according to claim 21, wherein the membrane thickness between the two "Electron-Dam" MEA may be in the range of 50-100 fold difference.

23. The nanobiomimetic supercapacitor according to claim 22, wherein the energy efficiency is 98%.

24. The nanobiomimetic supercapacitor according to claim 1, wherein the AGE result at the first 10 s is 3.88 kJ/kg $(cm^{-2})$ with a rate of 0.32 kJ/kg $(cm^{-2}) \cdot s^{-1}$ for a 1 $cm^2$ (MEA size) single supercapacitor in a symmetric configuration.

25. The nanobiomimetic supercapacitor according to claim 24, wherein the AVE value is 6.90 kJ/L with a rate of 0.57 kj/L·$s^{-1}$ for a 1 $cm^2$ (MEA size) single supercapacitor in a symmetric configuration.

26. The nanobiomimetic supercapacitor according to claim 25, wherein the AVE value is 7.71 kJ/L with a rate of 0.63 kj/L·$s^{-1}$ for a 0.5 $cm^2$ (MEA size) single supercapacitor in an asymmetric configuration.

27. The nanobiomimetic supercapacitor according to claim 26, wherein the discharge time is 11.8 hrs for the configuration.

28. The nanobiomimetic supercapacitor according to claim 27, wherein the specific capacity is 351.7 Ah/kg for the single 0.5 $cm^2$ supercapacitor configuration.

29. The nanobiomimetic supercapacitor according to claim 24, wherein the discharge time is more than 17 hrs for the configuration.

30. The nanobiomimetic supercapacitor according to claim 29, wherein the specific capacity is 798.5 Ah/kg for the 1 cm2 single supercapacitor configuration.

31. The nanobiomimetic supercapacitor according to claim 1, wherein the AGE result at the first 10 s is 4.77 kJ/kg $(cm^{-2})$ with a rate of 0.39 kJ/kg $(cm^{-2}) \cdot s^{-1}$ for a 0.5 $cm^2$ (MEA size) single supercapacitor in an asymmetric configuration.

32. The nanobiomimetic supercapacitor according to claim 1, wherein the AGE result at the first 10 s is 6.25 kJ/kg $(cm^{-2})$ with a rate of 0.54 kJ/kg $(cm^{-2}) \cdot s^{-1}$ for a 0.5 $cm^2$ (MEA size) single supercapacitor in an asymmetric configuration.

33. The nanobiomimetic supercapacitor according to claim 32, wherein the AVE value is 4.98 kJ/L with a rate of 0.43 kj/L·$s^{-1}$ for a 0.5 $cm^2$ (MEA size) single supercapacitor in an asymmetric configuration.

34. The nanobiomimetic supercapacitor according to claim 33, wherein it discharges 12 hrs.

35. The nanobiomimetic supercapacitor according to claim 34, wherein the specific capacity is 444.4 Ah/kg.

36. The nanobiomimetic supercapacitor according to claim 1, wherein it is catalyst free.

37. The nanobiomimetic supercapacitor according to claim 1, wherein it is an organic semiconductor has a switch at zero potential.

38. The nanobiomimetic supercapacitor according to claim 1, wherein the supercapacitor switches at zero potential, that the current is independent on the potential applied, which is nonpolarizable.

\* \* \* \* \*